United States Patent [19]
Fletcher et al.

[11] 3,977,831
[45] Aug. 31, 1976

[54] METHOD FOR DETECTING POLLUTANTS

[76] Inventors: James C. Fletcher, Administrator of the National Aeronautics and Space Administration, with respect to an invention of; Robert S. Rogowski, Hampton, Va.; Ralph R. Richards, Greenville, Ill.; Edmund J. Conway, Newport News, Va.

[22] Filed: Dec. 30, 1974

[21] Appl. No.: 537,480

[52] U.S. Cl. .......................... 23/232 E; 23/230 R; 23/232 R
[51] Int. Cl.² .................. G01N 25/00; G01N 27/62
[58] Field of Search ........ 23/230 R, 230 PC, 232 R, 23/232 E, 254

[56] References Cited
UNITED STATES PATENTS

| | | | |
|---|---|---|---|
| 3,528,779 | 9/1970 | Foutijn | 23/230 |
| 3,659,100 | 4/1972 | Anderson et al. | 23/230 X |
| 3,749,929 | 7/1973 | Wooten et al. | 23/232 |

OTHER PUBLICATIONS

Bowman et al., Science, vol. 154, 1966, pp. 1454–1456, Ozone–Induced Chemiluminescence of Organic Compounds.
Measurement of Atmospheric Ozone with the Chemiluminescent Method, Regener, J. of Geophysical Research, vol. 69, No. 18.
Emisson Spectra from Mixtures of Atomic Nitrogen & Organic Substances, Kiess et al., 7th Symposium on Comb., London, Oxford, 1958.
Chemiluminescent Material, Am. Cyanamid, Report No. 2, ARPA, No. 299, Amend D., Contract Nonr 42000(00).

*Primary Examiner*—Morris O. Wolk
*Assistant Examiner*—Michael S. Marcus
*Attorney, Agent, or Firm*—Howard J. Osborn; Wallace J. Nelson; John R. Manning

[57] ABSTRACT

A method for detecting and measuring trace amounts of pollutants of the group consisting of ozone, nitrogen dioxide and carbon monoxide in a gaseous environment wherein a sample organic solid material that will undergo a chemical reaction with the test pollutant is exposed to the test environment and thereafter, when heated in the temperature range of 100°–200°C., undergoes chemiluminescence that is measured and recorded as a function of concentration of the test pollutant and wherein the chemiluminescence of the solid organic material is specific to the pollutant being tested.

6 Claims, 3 Drawing Figures

METHOD FOR DETECTING POLLUTANTS

ORIGIN OF THE DISCLOSURE

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

The present invention relates to a method for detecting and measuring trace amounts of various pollutants in a gaseous environment. In one aspect, the invention relates to a method for detecting and measuring ozone; in another aspect, to a method of detecting and measuring trace amounts of nitrogen dioxide and in a third aspect, to a method of detecting and measuring carbon monoxide.

There are many known methods of determining the presence of trace impurities or pollutants in a gas. However, several of these methods require the use of devices that are cumbersome, expensive, or both, and there is a need for a simple and inexpensive reliable technique. This need is particularly acute in spacecraft and other installations where weight and bulkiness are of primary importance.

Accordingly, it is an object of the present invention to provide a simple and reliable technique for detecting and measuring trace amounts of various pollutants in a gas. It is a further object to provide such a technique which utilizes thin sheets or layers of organic solid materials which undergo chemical changes in the presence of selected pollutants and thereafter undergo chemiluminescence when heated.

Another object of the present invention is to provide lightweight, inexpensive pollution detectors with delayed readout capabilities.

BRIEF SUMMARY OF THE INVENTION

According to the present invention the foregoing and other objects are attainable by providing a thin layer of dry organic solid material that will undergo a chemical change in the presence of trace amounts of a specific pollutant in a gaseous environment and thereafter undergo chemiluminescence when heated. The total integrated light intensity measured during the heating cycle is a measure of the exposure to the concentration of the specific pollutant being tested.

The dry sensitive solid organic material suitable for detecting trace quantities of ozone according to the present invention is selected from the group consisting of rubrene, poly(ethylene 2, 6-naphthalene dicarboxylate) and 9,10 diphenyl anthracene. Organic solids that are specific for detecting trace amounts of nitrogen dioxide in a gaseous mixture are 3,5 diaminobenzoic acid and polyvinyl alcohol while the solid organic polyvinyl pyrrolidone is specific for carbon monoxide.

DETAILED DESCRIPTION

Figure 1:
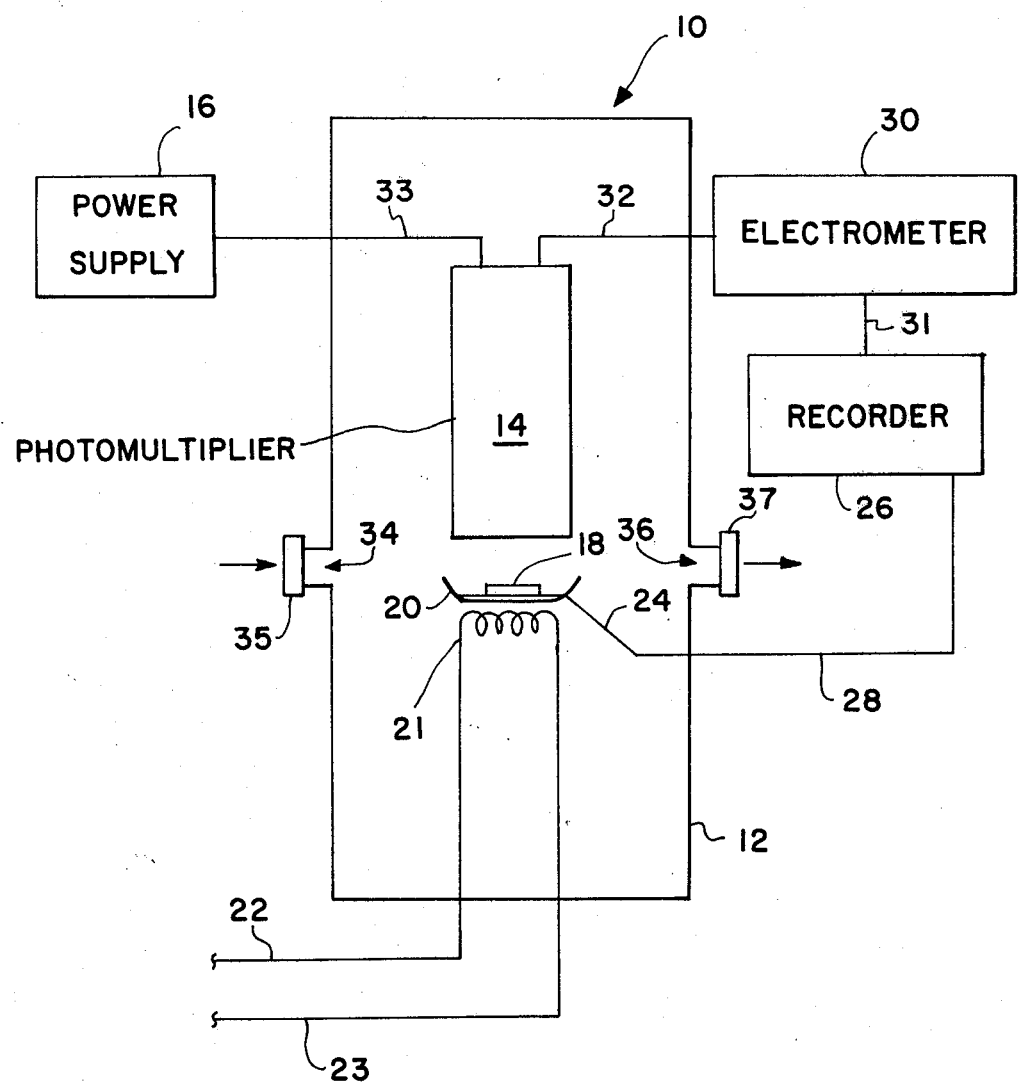
Figure 2:
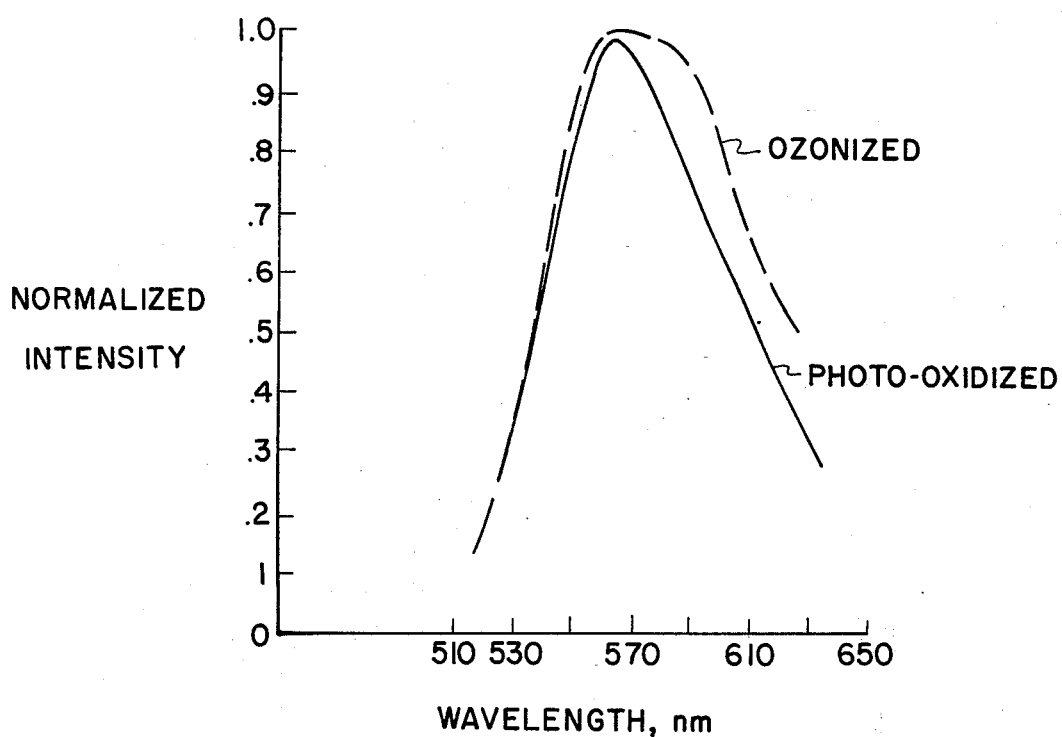
Figure 3:
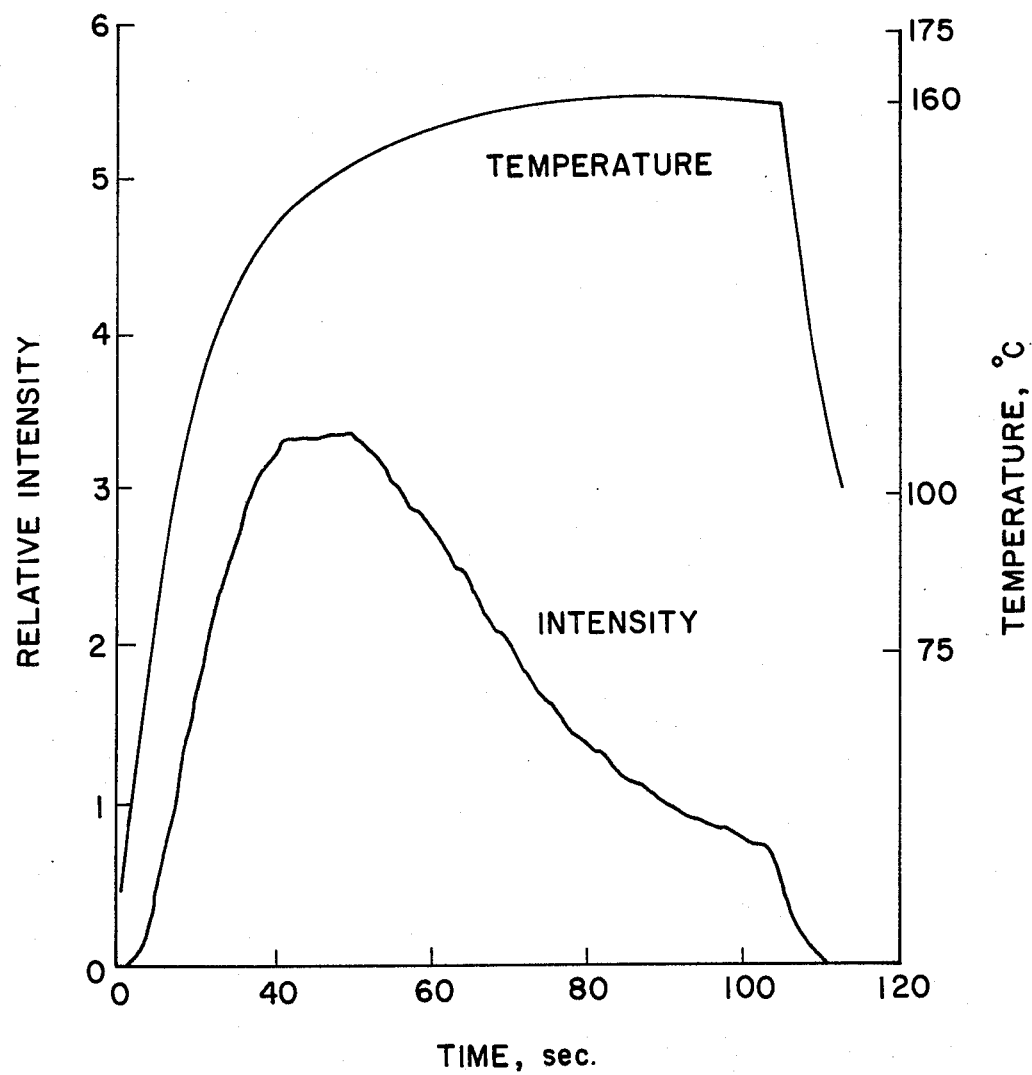

A more complete appreciation of the invention and many of the inherent advantages thereof will be more clearly understood by reference to the following detailed description when considered in connection with the specific examples and accompanying drawings wherein:

FIG. 1 is a schematic diagram of an apparatus useful for measuring the integrated chemiluminescent emission intensity from the exposed organic material according to the present invention, FIG. 2 illustrates the chemiluminescent spectra of ozonated and photo-oxidized rubrene, and FIG. 3 illustrates the chemiluminescent response curve for heated ozonated solid rubrene exposed to 0.15 ppm ozone.

Referring now to the drawings and more particularly to FIG. 1, there is shown the apparatus generally designated by reference numeral 10 for detecting and measuring chemiluminescence according to the present invention. Apparatus 10 includes a housing 12 containing a conventional photomultiplier tube 14 having yellow response and in electrical connection with a suitable power supply 16. A solid organic sample 18 that is to be measured for chemiluminescence is positioned in sample holder 20 adjacent heater element 21. Electric leads 22, 23 connect heater element 21 with a suitable power supply, not shown. A thermocouple 24 is in electrical connection with one of the pens on dual pen strip recorder 26 via lead wire 28. The other pen of recorder 26 is in electrical connection with an electrometer 30 via lead 31 to record the output received through lead 32 from photomultiplier 14.

Housing 12 is provided with a pair of openings in the sidewall thereof as designated by reference numerals 34 and 36 and shown closed, respectively, by covers 35 and 37. The various components of apparatus 10 are conventional, commercially available items, for example, photomultiplier 14 may be an EMI 9558 photomultiplier (green-yellow response) available from Gencom Division, VARIAN/EMI, 80 Express Street, Plainview, New York 11803; electrometer 30 an Elcor integrating electrometer available from Elcor, Inc., Falls Church, Virginia, and dual pen recorder 26 is an Electronik 194 from Honeywell, Inc., Fort Washington, PA 19034. Thermocouple 24 is a conventional chromel/alumel thermocouple soldered or otherwise thermally connected to sample holder 20 and electrically monitored by recorder 26 to continuously record the temperature of sample 18 as heated. When testing for ozone, sample 18 will be a thin layer of material selected from the group consisting of rubrene, poly(ethylene 2,6 napthalene dicarboxylate) and 9,10 diphenyl anthracene. When testing for nitrogen dioxide the sample will be a thin layer of material selected from the group consisting of 3,5 diaminobenzoic acid and polyvinyl alcohol and when testing for carbon monoxide the sample will be a thin layer of polyvinyl pyrrolidone.

The operation of the device described above is now believed apparent. In one application of the invention, the sample 18 to be tested for chemiluminescence is placed in sample holder 20 through one of the openings 34, 36 and the container cover replaced to close the container. In this test, the sample 18 would have previously been exposed to the test environment to permit the gas-solid reaction therewith. During exposure and testing of sample 18 care is exercised to prevent exposure of the sample to light to minimize reaction of the sample with oxygen in presence of ultraviolet radiation since some of the sample materials are known to produce chemiluminescence when reacted with oxygen in the presence of light.

The exposed solid sample 18 is heated to 100°–200°C. by heater element 21 and light emitted by chemiluminescence, is detected by photomultiplier 14, amplified by electrometer 30 and recorded simultaneously with the temperature on dual pen recorder 26.

The light output from the sample rises to a maximum in a few seconds as shown in the graph of FIG. 2 for ozonated rubrene and then gradually decays to zero in approximately two minutes.

The total integrated light intensity measured during the heating cycle is a measure of the exposure to the pollutant concentration being tested in the gas sample. Thus, the present invention may be used to test and measure even trace quantities of the test pollutants since the concentration thereof is integrated over the exposure time and the chemiluminescent light is released in a very short period of time during the heating process. The limits on detection of trace amounts of the pollutants can therefore be increased by simply increasing the exposure time of the solid to the gas with no increase in the heating cycle being required for measuring the light output.

In a similar operation of the present invention an unexposed sample 18 would be positioned within sample holder 20 with covers 35 and 37 being removed and a test gaseous medium pumped through housing 12 via openings 34, 36 to expose sample 18. After the desired time interval of exposure, the gas flow is stopped and heater element 21 actuated to heat the sample with the chemiluminescence of sample 18 being recorded, as before.

Since the sample organic solid material is specific to the pollutant being tested, the presence of other gaseous constituents do not interfere with the present invention. Thus, the presence of $H_2S$, CO, NO, $NO_2$, $SO_2$ and $N_2$ do not interfere with the test of ozone when the sample organic solid is selected from rubrene, poly(ethylene 2,6 naphthalene dicarboxylate) and 9,10 diphenyl anthracene. Also, when the sample organic solid is selected from 3,5 diaminobenzoic acid and polyvinyl alcohol the test is specific for $NO_2$ and various quantities of $SO_2$, CO, NO, $H_2S$, $O_2$ and $N_2$ in the gas will produce no light and will not degrade the sensitivity of the sample to $NO_2$. The same specificity of polyvinyl pyrrolidone to CO prevents interference of this reaction with other constituents in a gaseous mixture.

The system described is dry in the sense that no liquid solutions are required as in some known tests for these specific pollutants. The process as described hereinabove is capable of detecting trace quantities of the pollutants using only thin layers of the sensitive organic solid material. For example, ozone in the 1–10 ppm range (in nitrogen) have been detected using only $10^{-4}$ g of rubrene with a signal to noise ratio in excess of 10:1 after four minutes exposure to the ozone-nitrogen mixture. This sensitivity can be further increased using longer exposure times since the concentration measurement is integrated over the exposure time.

As discussed hereinabove, it is not necessary to locate the solid state sensitive material in the readout instrument. Samples could be placed at various locations for monitoring average pollutant concentrations over a period of hours or days. These samples could be apart from the readout with a single instrument to eliminate the expense of several electron packages. Also, the solid sensitive samples may be used for personal monitors to detect total exposure to the specific pollutants in much the same way that film badges are presently used to monitor individual radiation exposure. This capability would be possible while still maintaining the sample protected from ambient light by enclosing the sample in a small container and utilizing a small hand pump, or the like, to divert ambient air through the container to contact and expose the sample. Also, the solid organic samples described herein could be employed on thin film strips and adapted for controlled multiple exposure modes on a cassette-type pollution recording system. This latter packaging arrangement might prove particularly useful in aircraft, space flight and the like, where controlled time exposures to unknown gaseous environments could be tested and read out at postflight evaluation at a later date or by onboard readout equipment being signaled to remote stations, in a conventional manner.

The materials for making the solid sensitive organic samples are inexpensive due to the small quantities needed, costing less than one cent per exposure, and capital equipment for accurate measurement of exposures can be centrally located and efficiently process hundreds of exposures per day.

Rubrene samples suitable for use in the present process have been prepared by spraying a solution of 10% rubrene in benzene onto small flexible aluminum squares. The samples were allowed to dry and were maintained under a nitrogen atmosphere and heated until the inherent chemiluminescence was absent before exposure to controlled concentration of ozone. Samples of rubrene have also been prepared by subliming rubrene in vacua onto flexible aluminum strips. These samples were then exposed to known concentrations of ozone from 0.03 to 0.30 ppm over an exposure range of 0 to 60 minutes and measured by the apparatus shown in FIG. 1 to confirm the operation of the present invention.

Thin sheets of the other solid sample organic materials discussed hereinbefore are also readily available and can be conventionally adhered to flexible strips adaptable for use in the present process. Poly(ethylene 2,6 naphthalene dicarboxylate), for example, is available in film strips as thin as 0.254 mm.

Since some of the solid organic sample materials will luminesce when exposed to light, all samples should be initially heated to the 100°–200°C. cycle and maintained in darkness while cooled and during subsequent exposure and testing to eliminate false readings.

Although the invention has been described relative to use of precise equipment and with specific illustrative examples, it is not so limited. There are obviously many modifications and variations of the present invention that will be readily apparent to those skilled in the art in the light of the above teachings. For example, one or all of the specific solid organic sample materials may be spaced along the same film strip so as to give exposure thereof simultantously or sequentially to the same test gas. Also, other materials than those specifically disclosed may prove specific for one of the test pollutants discussed and other materials may subsequently be found specific for other pollutants not discussed herein. It is therefore to be understood that the invention may be practiced otherwise than as specifically described herein within the scope of the appended claims.

What is claimed as new and desired to be secured by Letter Patent of the United States is:

1. A method for detecting and measuring trace amounts of pollutants of the group consisting of ozone, nitrogen dioxide and carbon monoxide in a gaseous environment comprising:
    selecting a sample organic solid having the inherent property characteristics of chemically reacting with the gaseous pollutant being tested and thereafter undergoing chemiluminesence when heated, exposing the selected sample organic solid material to an environment suspected of containing at least one of said pollutants, and reacting said solid material with said one of said pollutants, heating the reacted sample organic solid material in the temperature range of 100°–200°C. for approximately one minute, detecting and measuring the light output from the sample solid organic material during the heating cycle, recording the total integrated light intensity measured during the heating cycle as a concentration of the specific pollutant being tested.

2. The method of claim 1 wherein the atmospheric pollutant tested is ozone and the sample organic solid is selected from the group consisting of rubrene, poly(ethylene 2,6 naphthalene dicarboxylate), and 9,10 diphenyl anthracene.

3. The method of claim 2 wherein the sample organic solid is a thin vapor deposited rubrene layer.

4. The method of claim 1 wherein the atmospheric pollutant tested is nitrogen dioxide and the sample organic solid is selected from the group consisting of 3,5 diaminobenzoic acid and polyvinyl alcohol.

5. The method of claim 1 wherein the atmospheric pollutant tested is carbon monoxide and the organic solid is polyvinyl pyrrolidone.

6. The method of claim 1 wherein the atmospheric pollutant tested is ozone and the exposure to the solid organic solid is in the absence of light.

* * * * *